US012778462B2

(12) United States Patent
Chae et al.

(10) Patent No.: US 12,778,462 B2
(45) Date of Patent: Nov. 3, 2026

(54) CONTINUOUS BLOOD GLUCOSE MEASUREMENT APPARATUS

(71) Applicant: I-SENS, INC., Seoul (KR)

(72) Inventors: Kyoung Chul Chae, Seoul (KR); Hyun Ho Choi, Seoul (KR); Young Jea Kang, Seoul (KR); David Lee, Seoul (KR); Su Jin Lee, Seoul (KR)

(73) Assignee: I-SENS, INC., Seoul (KR)

( * ) Notice: Subject to any disclaimer, the term of this patent is extended or adjusted under 35 U.S.C. 154(b) by 884 days.

(21) Appl. No.: 17/908,905

(22) PCT Filed: Mar. 2, 2021

(86) PCT No.: PCT/KR2021/002537
§ 371 (c)(1),
(2) Date: Sep. 1, 2022

(87) PCT Pub. No.: WO2021/177686
PCT Pub. Date: Sep. 10, 2021

(65) Prior Publication Data
US 2024/0197209 A1 Jun. 20, 2024

(30) Foreign Application Priority Data
Mar. 3, 2020 (KR) ........................ 10-2020-0026756

(51) Int. Cl.
*A61B 5/145* (2006.01)
*A61B 5/00* (2006.01)

(52) U.S. Cl.
CPC ...... *A61B 5/14532* (2013.01); *A61B 5/14503* (2013.01); *A61B 5/6848* (2013.01)

(58) Field of Classification Search
CPC ............ A61B 5/14532; A61B 5/14503; A61B 5/6848; A61B 5/150022; A61B 5/150427; A61B 5/1473
See application file for complete search history.

(56) References Cited

U.S. PATENT DOCUMENTS 9,393,043 B2 7/2016 Matsumoto et al.
10,371,693 B2 8/2019 Lee et al.
(Continued)

FOREIGN PATENT DOCUMENTS

CN 203314969 12/2013
CN 104168826 11/2014
(Continued)

OTHER PUBLICATIONS

Office Action dated Sep. 10, 2024 for Japanese Patent Application No. 2022-552915 and its English translation from Global Dossier.
(Continued)

*Primary Examiner* — Christian Jang
(74) *Attorney, Agent, or Firm* — WOMBLE BOND DICKINSON (US) LLP

(57) ABSTRACT

The present disclosure relates to a continuous blood glucose monitoring device, and provides a continuous blood glucose monitoring device, which has an incision area formed by means of a guide needle, in a state in which a body-attaching unit is insertively attached to a body, so as not to encompass at least a part of a region of a sensing area formed in a sensor member, so that the incision part is not formed near the sensing area, and thus the present invention can prevent a decrease in a blood glucose monitoring value that occurs because of the incision part so as to detect an accurate blood glucose monitoring value from an initial operation stage, and adjusts an insertion depth of the guide needle through an applicator when the body-attaching unit is insertively attached to the human body, so as to adjust the separation distance between the incision part and the sensing area by means of the guide needle, thereby improving blood glucose monitoring accuracy.

10 Claims, 12 Drawing Sheets

(56) References Cited

U.S. PATENT DOCUMENTS

| | | | | |
|---|---|---|---|---|
| 2005/0215871 | A1 | 9/2005 | Feldman et al. | |
| 2008/0114280 | A1 | 5/2008 | Stafford | |
| 2014/0005509 | A1 | 1/2014 | Bhavaraju et al. | |
| 2016/0058470 | A1 | 3/2016 | Peterson et al. | |
| 2016/0331283 | A1* | 11/2016 | Rao | A61B 5/14503 |
| 2017/0112534 | A1* | 4/2017 | Schoonmaker | A61B 5/6833 |
| 2018/0199873 | A1 | 7/2018 | Wang et al. | |
| 2018/0235520 | A1* | 8/2018 | Rao | A61B 5/6823 |
| 2021/0169518 | A1* | 6/2021 | Shimizu | A61B 5/1473 |

FOREIGN PATENT DOCUMENTS

| | | |
|---|---|---|
| CN | 106461671 | 2/2017 |
| JP | 2019-500064 | 1/2019 |
| JP | 2019-507613 | 3/2019 |
| KR | 10-2018-0132557 | 12/2018 |
| KR | 10-2019-0025208 | 3/2019 |
| WO | 2009/024522 | 2/2009 |
| WO | 2016/191302 | 12/2016 |
| WO | 2018/194281 | 10/2018 |
| WO | 2018/222012 | 12/2018 |
| WO | 2020/027420 | 2/2020 |
| WO | 2020/027422 | 2/2020 |
| WO | 2020/027423 | 2/2020 |
| WO | 2020/027424 | 2/2020 |

OTHER PUBLICATIONS

Extended European Search Report dated Jan. 11, 2024 for European Patent Application No. 21765062.1.

International Search Report for PCT/KR2021/002537 mailed on Jun. 9, 2021 and its English translation from WIPO (now published as WO 2021/177686).

Written Opinion of the International Searching Authority for PCT/KR2021/002537 mailed on Jun. 9, 2021 and its English translation by Google Translate (now published as WO 2021/177686).

Office Action (1st) dated Jun. 30, 2025 for Chinese Patent Application No. 202180017003.4 and its English translation from Global Dossier.

Notice of Allowance dated Jan. 9, 2026 for Chinese Application No. 202180017003.4 and its English translation by Google Translate.

* cited by examiner

[Fig. 1]
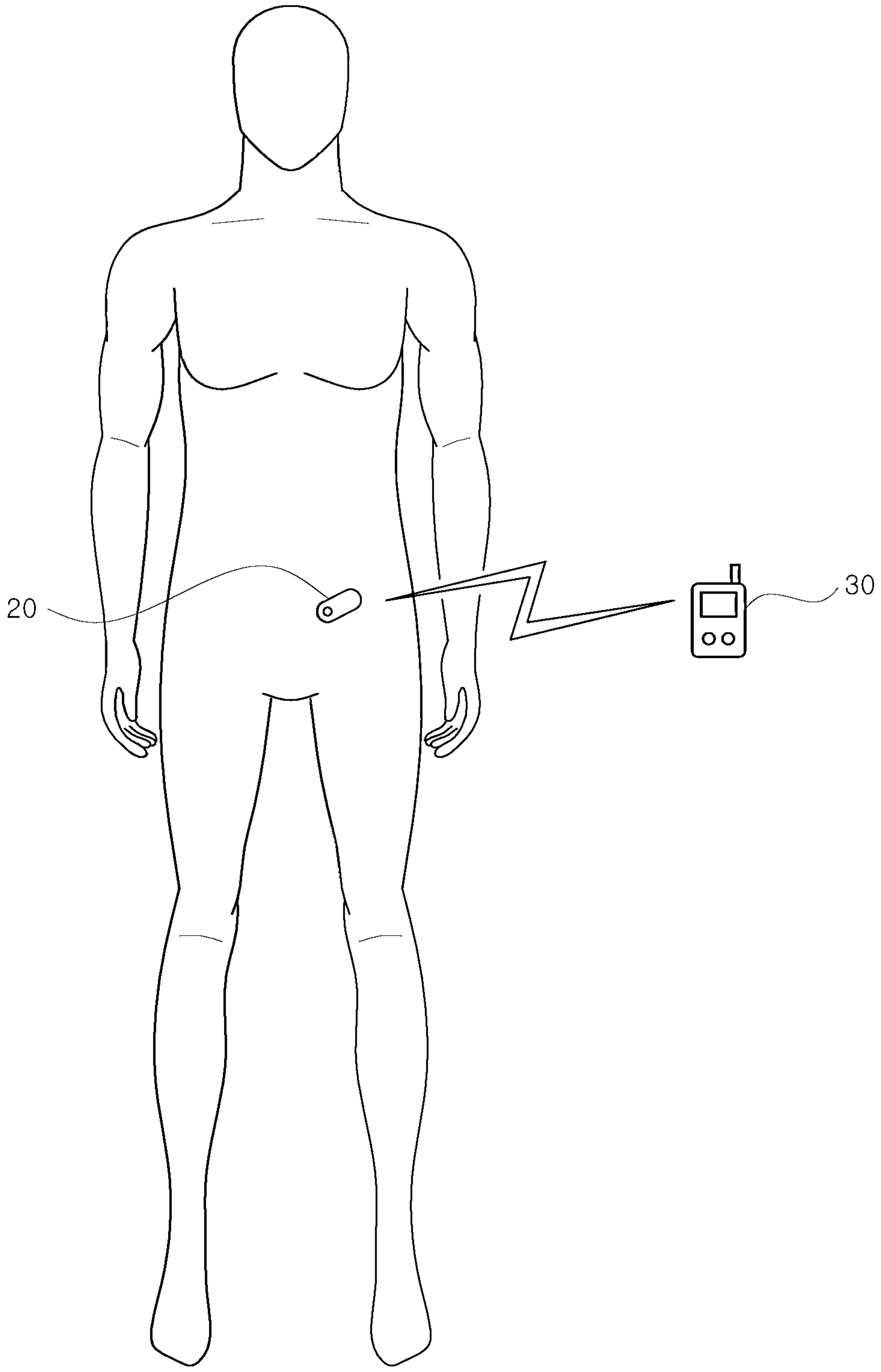

[Fig. 2]
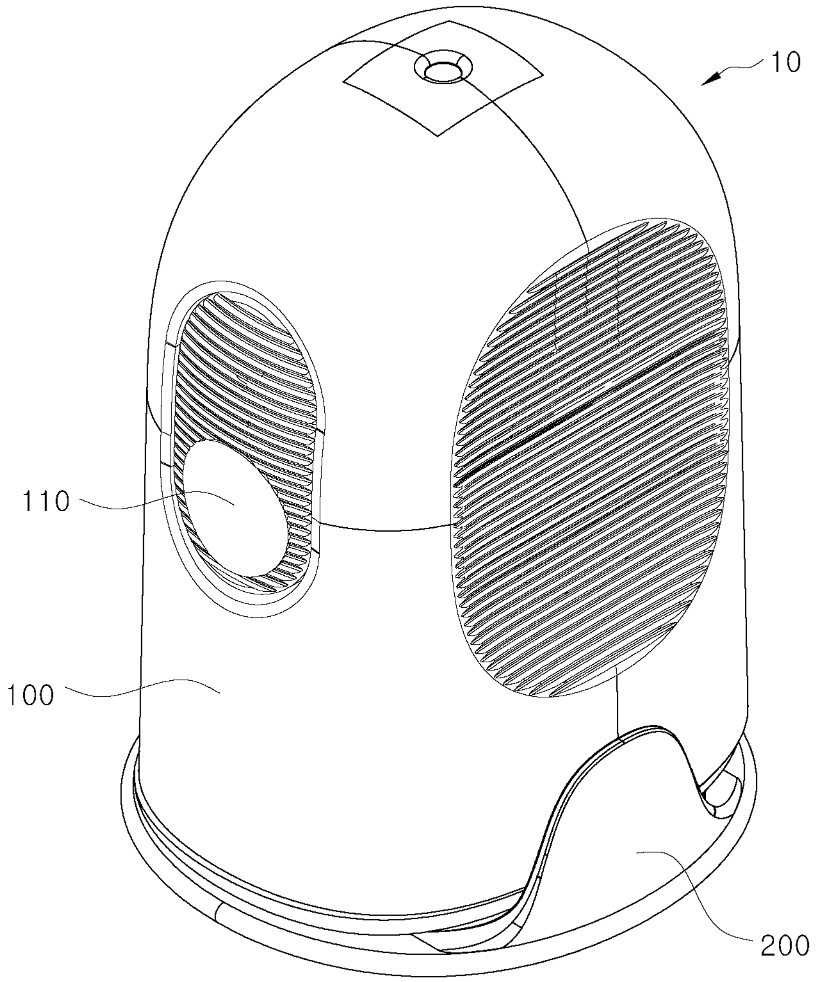

[Fig. 3]
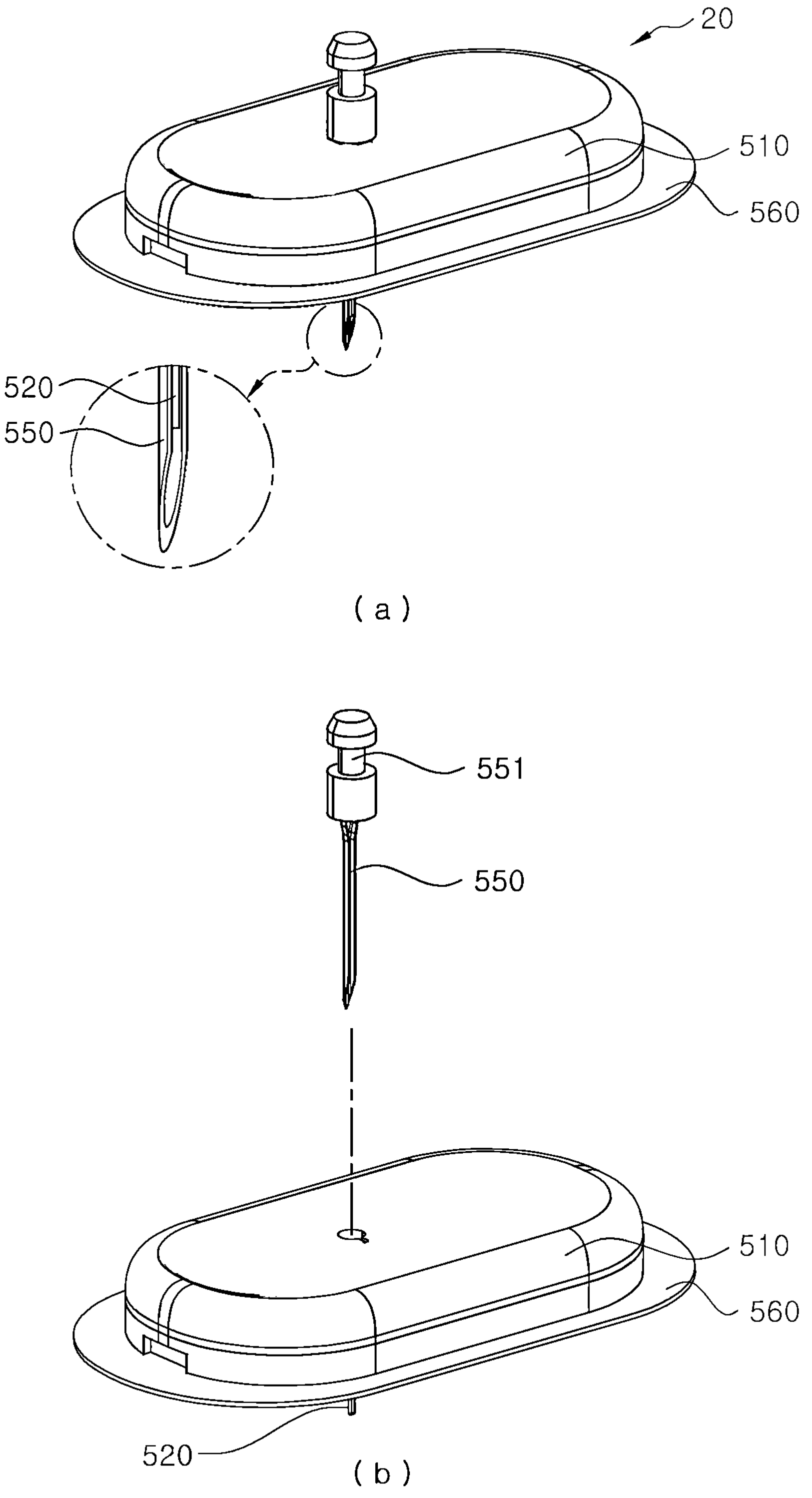

[Fig. 4]
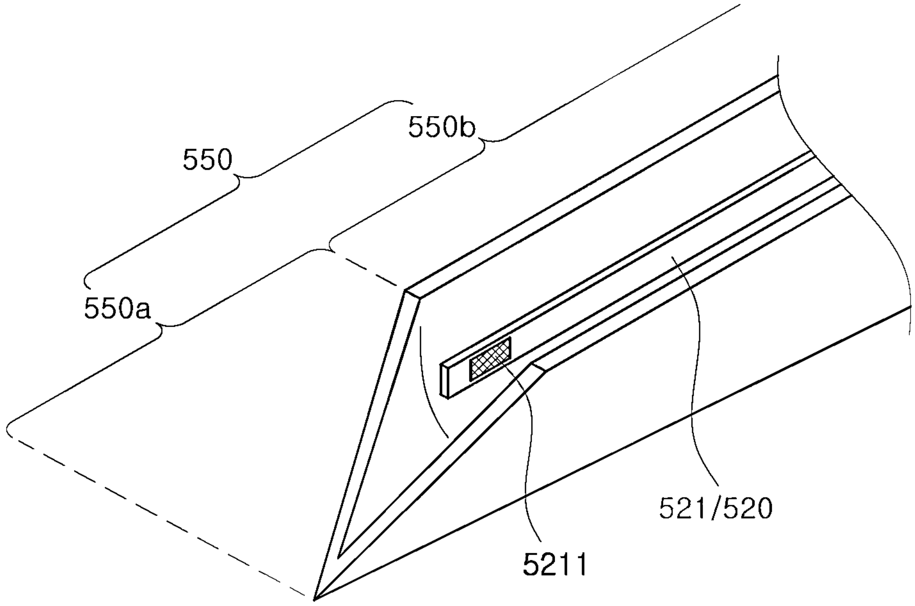

[Fig. 5]
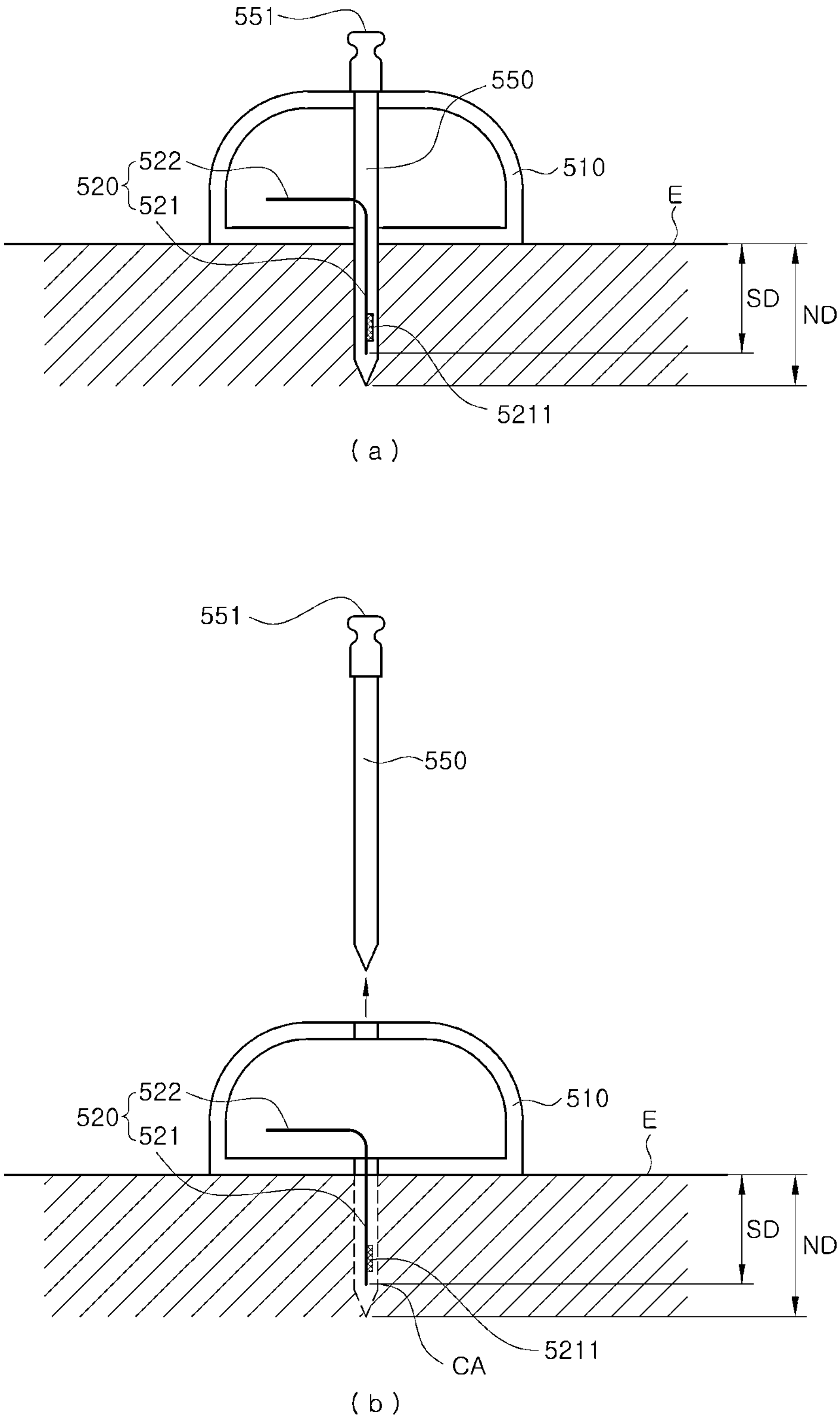

[Fig. 6]
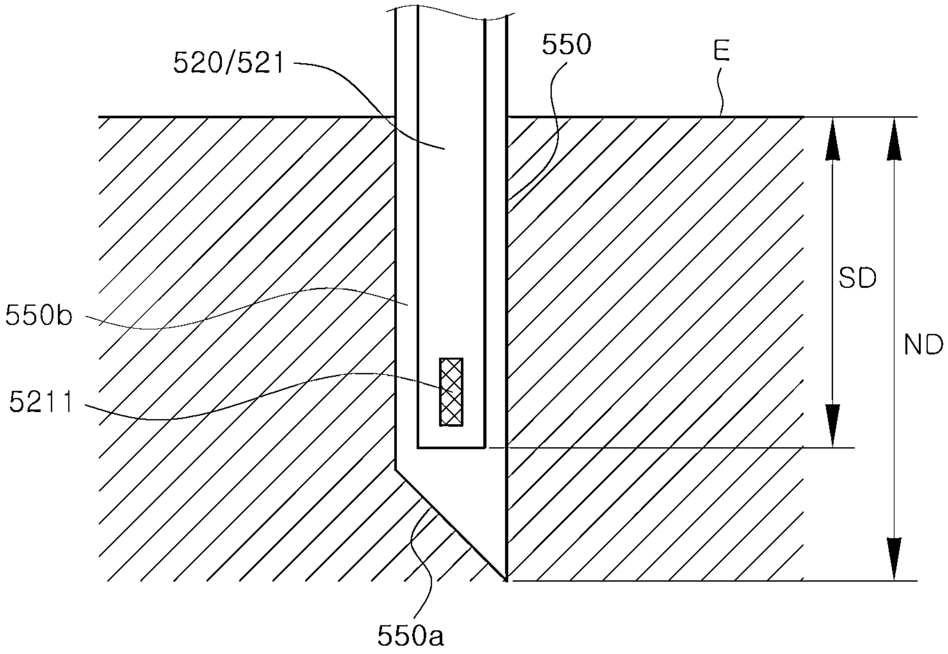

[Fig. 7]
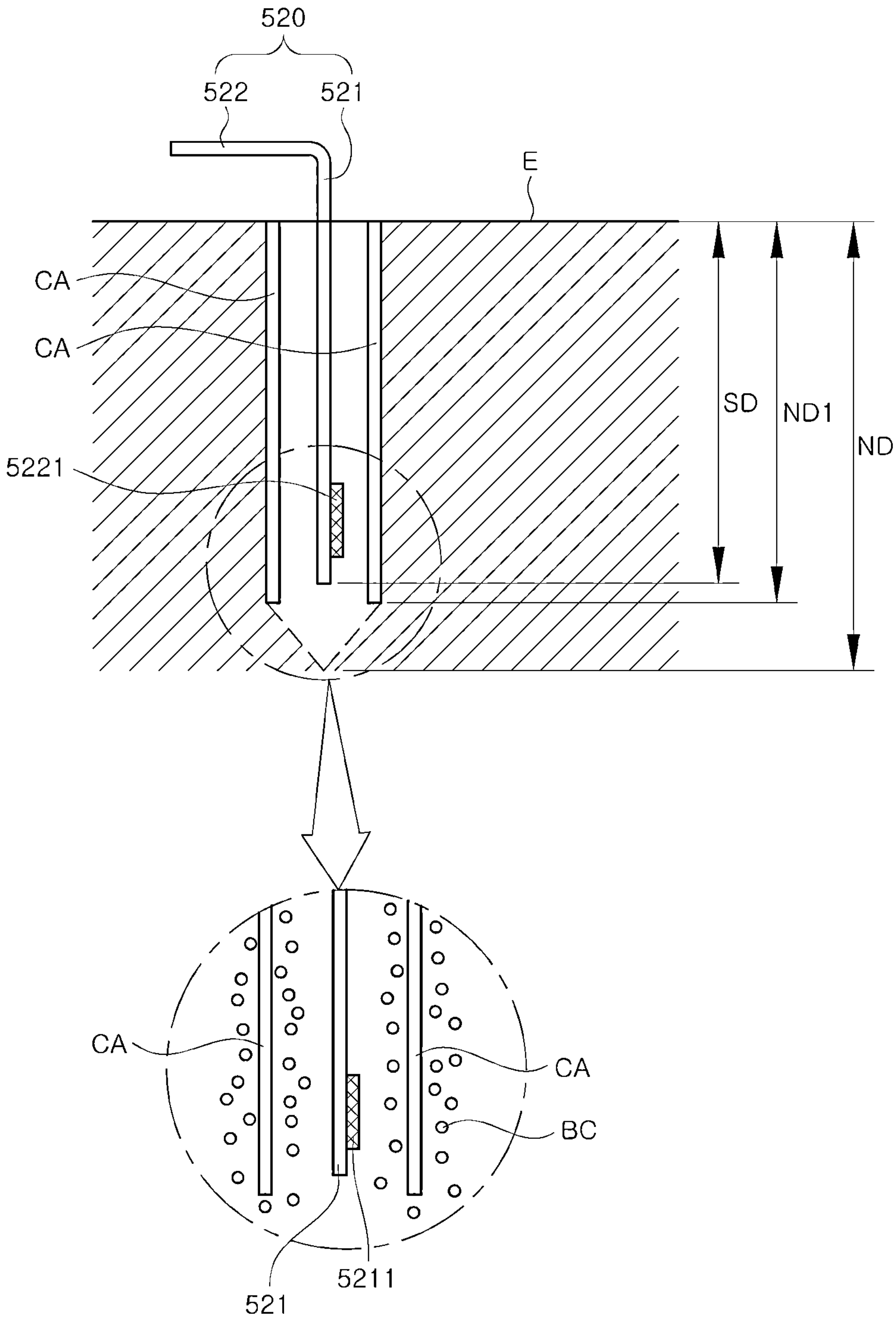

[Fig. 8]
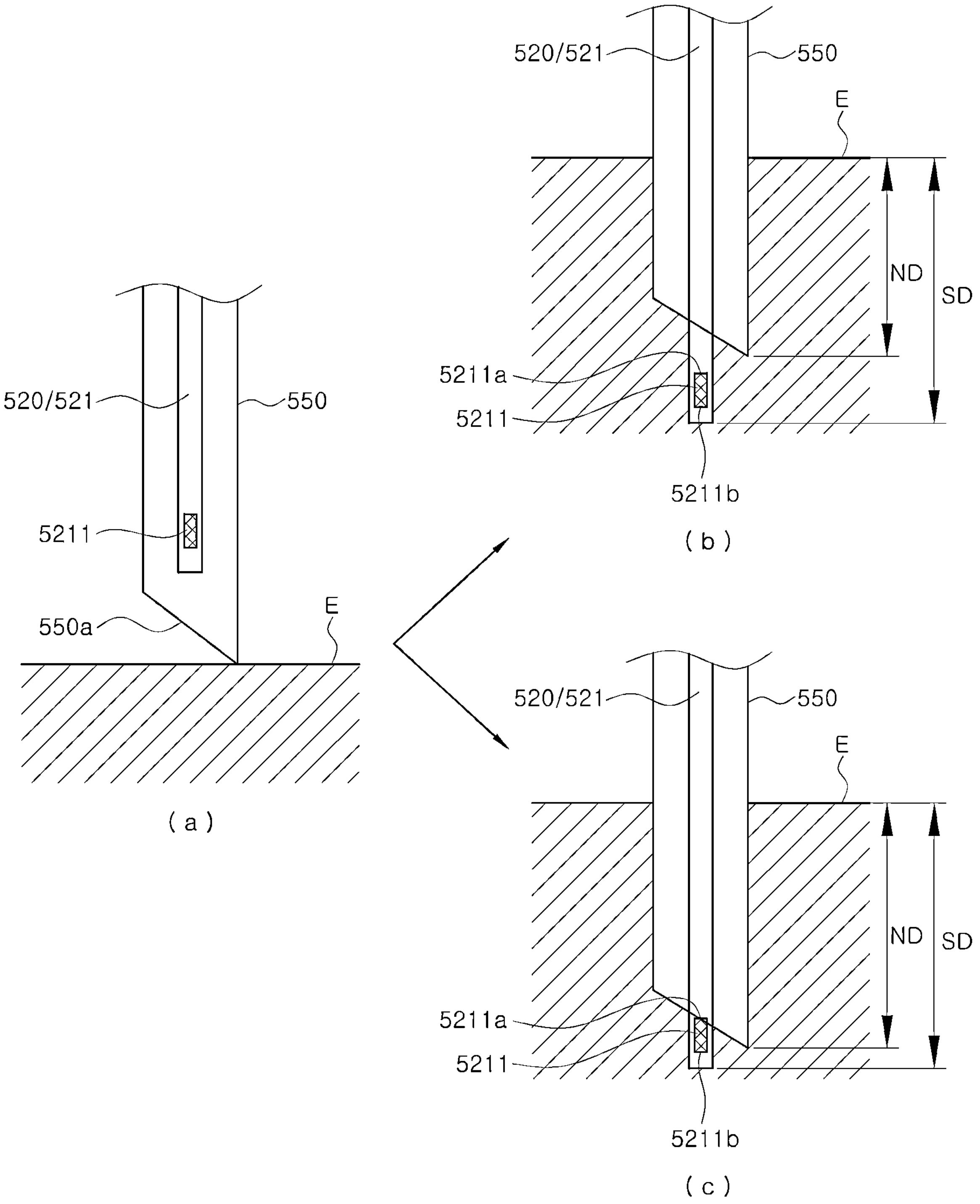

[Fig. 9]
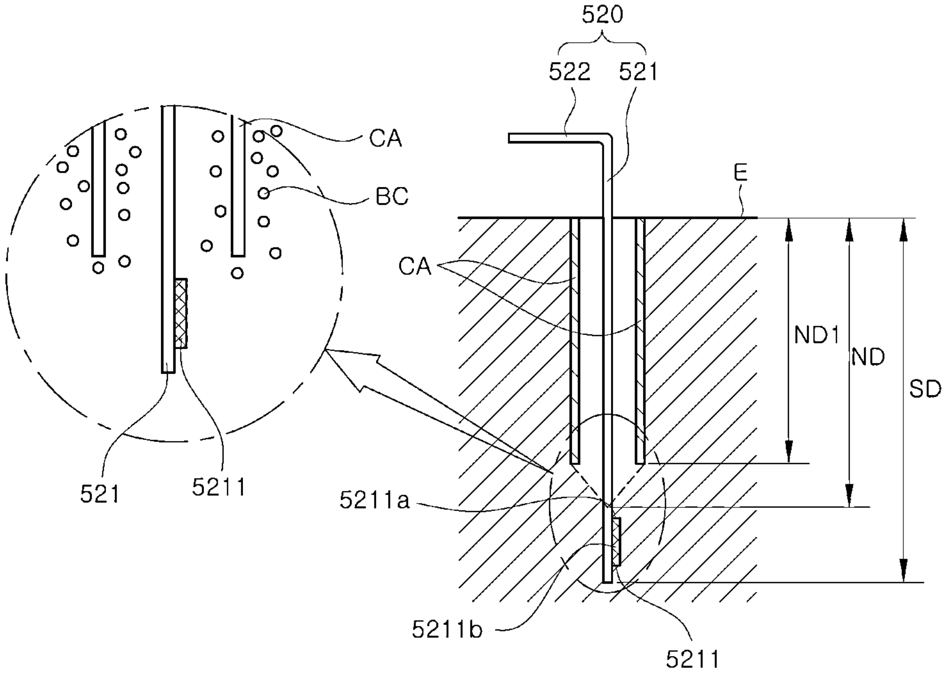
( a )
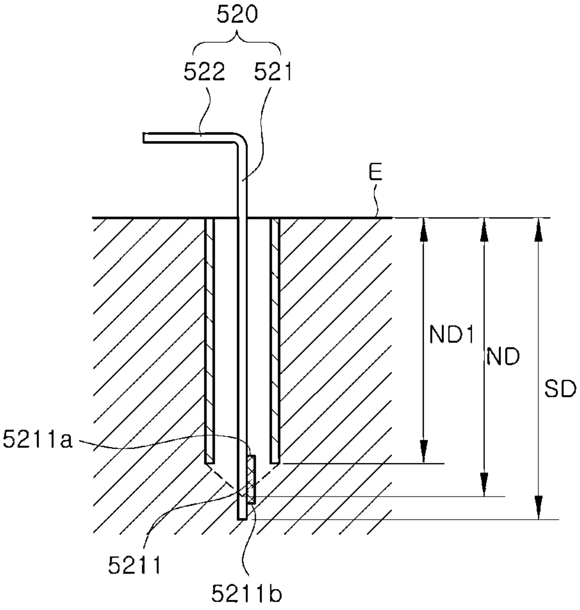
( b )

[Fig. 10]
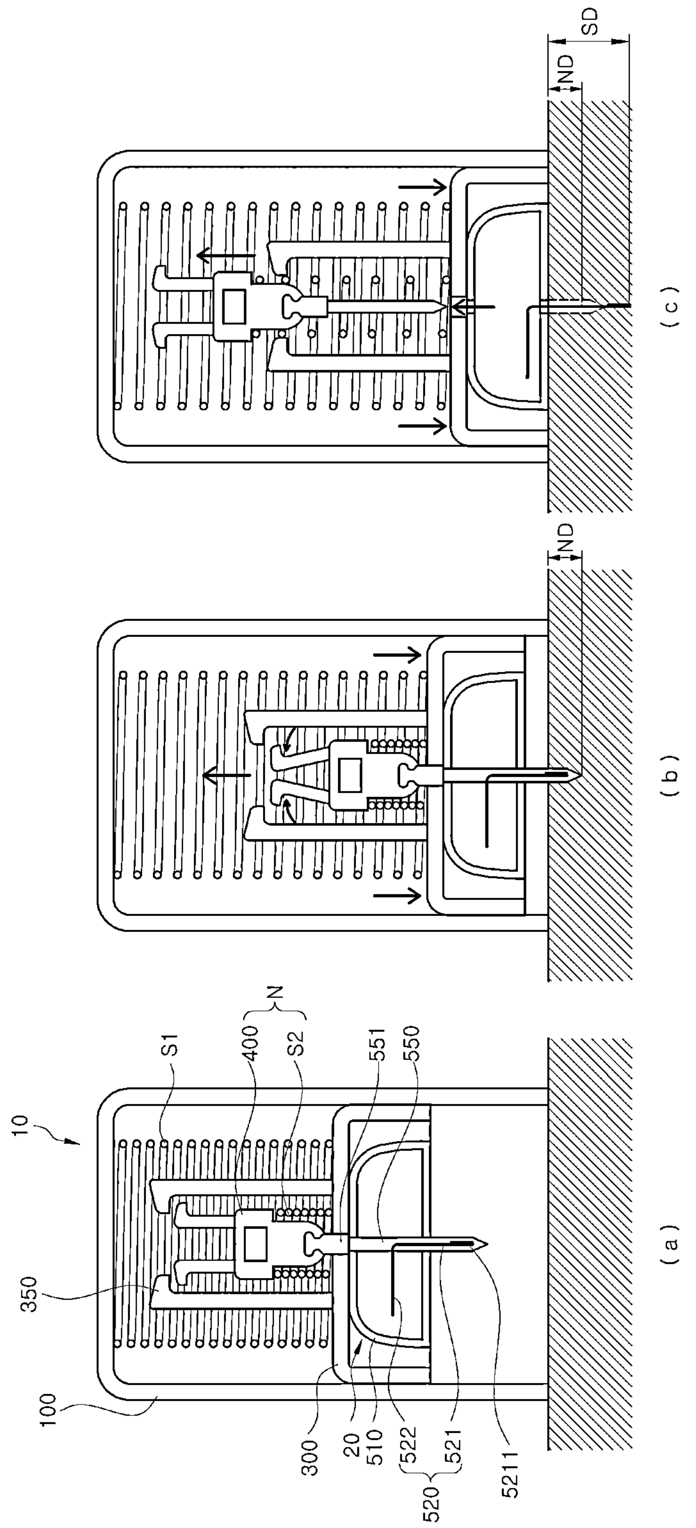

[Fig. 11]
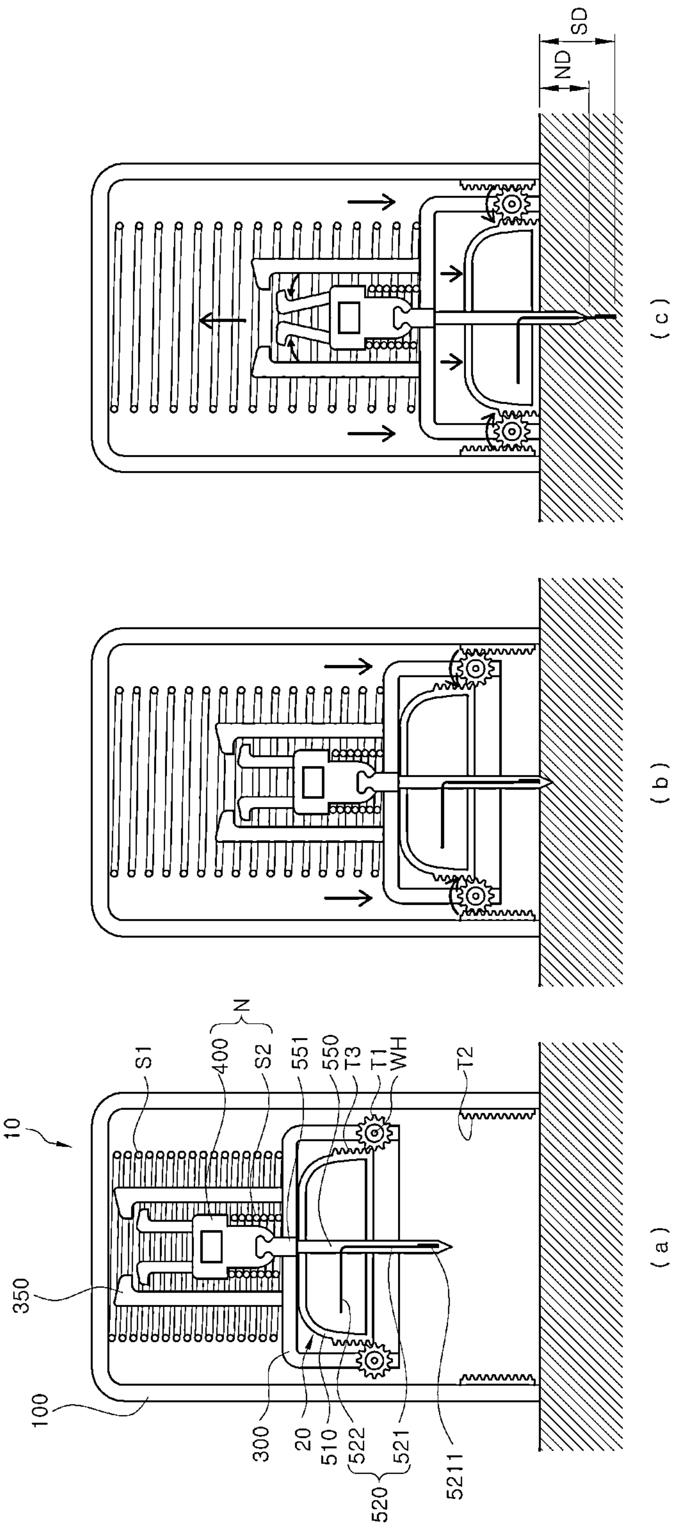

[Fig. 12]
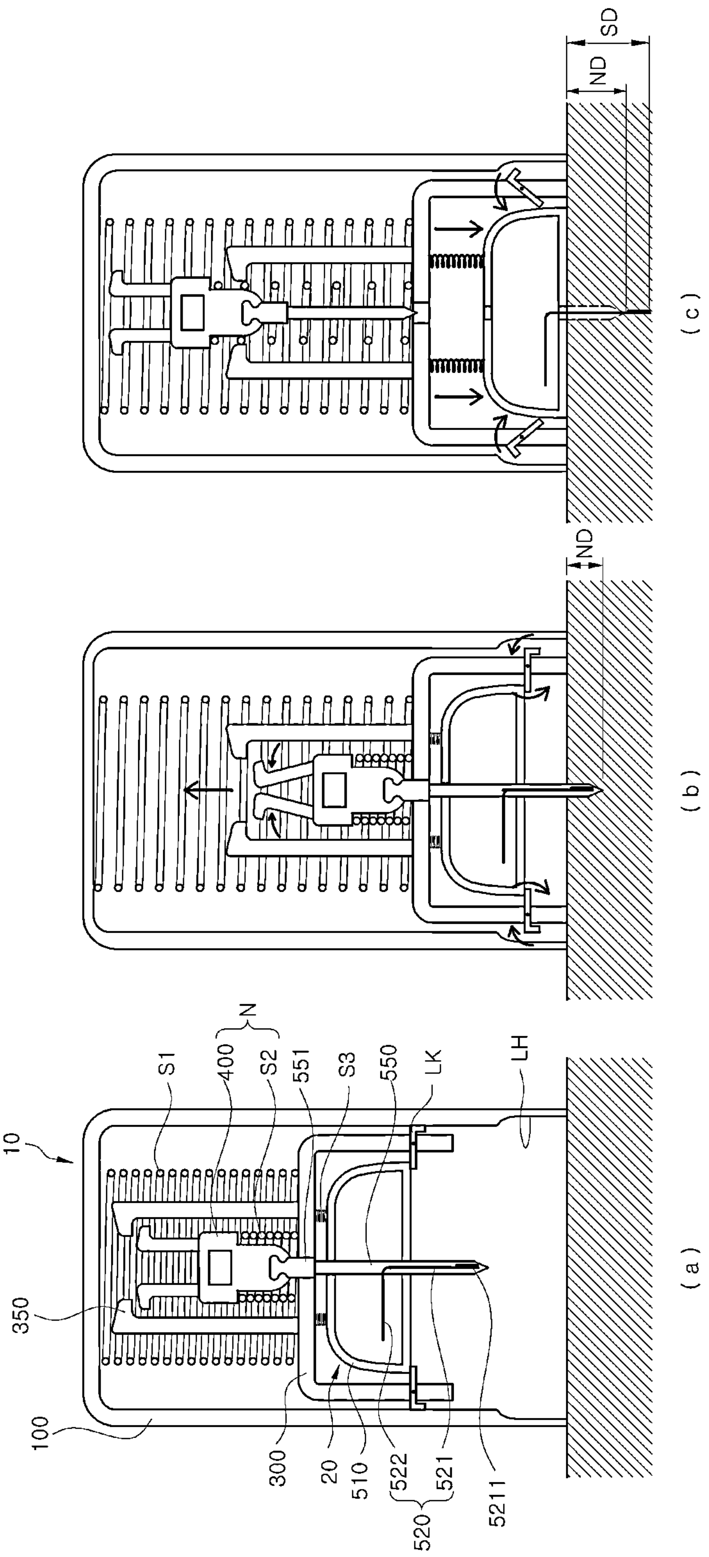

CONTINUOUS BLOOD GLUCOSE MEASUREMENT APPARATUS

CROSS-REFERENCE TO RELATED APPLICATIONS

The present application is the U.S. National Phase of PCT Application No. PCT/KR2021/002537 filed on Mar. 2, 2021, which claims the priority to Korean Patent Application No. 10-2020-0026756 filed on Mar. 3, 2020, the entire contents of which are incorporated herein by reference.

TECHNICAL FIELD

The present disclosure relates to a continuous blood glucose measurement apparatus. More specifically, the present disclosure relates to a continuous blood glucose measurement apparatus in which, by forming an incised portion by a guide needle so that the incised portion by the guide needle does not cover at least a partial area of a sensing area formed at a sensor module in a state in which a body attachable unit is inserted and attached to a body, the incised portion is not formed adjacent to the sensing area, accordingly a phenomenon of lowering a blood glucose measurement value caused by the incised portion can be prevented, thereby detecting an accurate blood glucose measurement value from the early stage of operation, and by adjusting an insertion depth of the guide needle through an applicator in a process of inserting and attaching the body attachable unit to the body, a separation distance between the incised portion by the guide needle and the sensing area are adjusted, thereby improving a blood glucose measurement accuracy.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels at home.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

Additionally, the blood-collecting glucose monitoring system performs the glucose measurement by collecting blood by pricking a pain-sensitive fingertip with a needle by the diabetes patients themselves, and therefore, the blood collecting process may cause pain and aversion. To minimize such pain and aversion, research and development regarding the CGMSs, which can continuously measure glucose levels by inserting a needle-shaped sensor into a portion of the human body, such as the belly or an arm, which is less pain sensitive, have been undertaken, and furthermore, research and development of non-invasive glucose monitoring systems for measuring glucose without collecting blood have been actively undertaken.

Over the past 40 years, non-invasive glucose monitoring systems have been studied regarding various methods of measuring glucose without collecting blood, for example, optical methods, electrical methods, exhalation measurement methods, and the like. *Cygnus* Corporation, Redwoo City, Calif., U.S.A, has developed and launched the Glucowatch® G2 Biographer, a wrist watch type, using reverse iontophoresis, but the sales of this product were stopped in 2007, because of many problems, such as skin stimulation issues and qualification approval issues, malfunction caused by sweating, and low reliability in measurement of hypoglycemia comparing with hyperglycemia. Although a variety of non-invasive glucose monitoring techniques have been introduced and reported to date, there have been no practical uses due to low reliability or accuracy.

A continuous glucose monitoring system includes a sensor module inserted and attached to the skin of the human body and measuring a blood glucose level by extracting body fluid, a transmitter transmitting the blood glucose level measured by the sensor module to a terminal, the terminal outputting the received blood glucose level, and any other appropriate component. The sensor module includes a needle-shaped sensor probe for insertion into subcutaneous fat to extract interstitial fluid and any other appropriate component. A separate applicator for attaching the sensor module to the body is used.

Those continuous glucose monitoring systems are manufactured to have a wide variety of types depending on their manufacturers, and are used in a variety of methods. However, the most of the continuous glucose monitoring systems are manufactured and distributed as a type that a one-time use sensor module is attached to the human body using an applicator, and an adhesive tape is attached to an outer housing of the sensor module so that the sensor module can be attached to the human body. If the sensor module is attached to the human body skin through the applicator according to this structure, a state that the sensor module is attached to the human body skin is maintained by the adhesive tape, and, the blood glucose is periodically and continuously measured in this state.

Because a part inserted into the skin among a sensor member of the sensor module is formed of a soft material, a guide needle is provided to guide the process of inserting the sensor member into the skin. That is, the part inserted to the skin among the sensor member is arranged to outwardly protrude from the bottom surface of an outer housing of the sensor module, the guide needle is arranged to surround a part of the sensor member inserted into the skin from the outside, and, during the process in which the sensor module is attached to the skin through the applicator, the guide needle is inserted into the skin together with the sensor member. When the skin insertion process of the sensor member is completed, the guide needle is configured to be removed from the skin by the applicator.

Such a continuous blood glucose measurement apparatus generally exhibits a characteristic that, when the sensor module is attached to the body, the blood glucose measurement accuracy is lowered in the initial state of operation, and, after a considerable amount of time has elapsed, the accuracy is improved. Although various studies are being conducted to solve the problem of the deterioration of the initial measurement accuracy, there are still no satisfactory research results.

SUMMARY

Technical Problem

The present disclosure is invented to solve problems in conventional technique, and the purpose of the present disclosure is for providing a continuous blood glucose measurement apparatus in which, by forming an incised portion by a guide needle so that the incised portion by the guide needle does not cover at least a partial area of a sensing area formed at a sensor module in a state in which a body attachable unit is inserted and attached to a body, the incised portion is not formed adjacent to the sensing area, and accordingly a phenomenon of lowering a blood glucose measurement value caused by the incised portion can be prevented, thereby detecting an accurate blood glucose measurement value from the early stage of operation.

Another purpose of the present disclosure is for providing a continuous blood glucose measurement apparatus in which, by adjusting an insertion depth of the guide needle through an applicator in a process of inserting and attaching the body attachable unit to the body, a separation distance between the incised portion by the guide needle and the sensing area are adjusted, thereby improving a blood glucose measurement accuracy.

Solution to Problem

The present disclosure provides a continuous glucose measurement apparatus comprising: a body attachable unit configured to be insertedly attachable to a body to periodically measure blood glucose; and an applicator configured to insert and attach the body attachable unit to the body according to manipulation of a user, wherein the body attachable unit comprises: a sensor module configured to be insertable into the body, wherein a sensing area to react with the blood glucose in the body is formed at one side of the sensor module, and a guide needle arranged to cover an outside of the sensor module, and configured to, after being inserted into the body together with the sensor module, be extracted and removed from the body, wherein an incised portion incised by the guide needle in the body is formed not to surround at least a part of the outside of the sensing area.

At this time, in a body insertion process, the guide needle may be inserted to the body before or at the same time as the sensor module is inserted to the body.

Additionally, the sensor module may comprise a sensor probe portion formed to be elongated along a body insertion direction so that at least a partial section of the sensor probe portion is insertable into the body, and the sensing area may be formed at an end part of the sensor probe portion.

Further, the guide needle may have a shape of covering an outside of the sensor probe portion, and the guide needle may be configured to be extracted and removed from the body after being inserted to a shallower depth than the sensor probe portion.

In addition, an end of the guide needle may be inserted to a depth closer to a skin surface than a maximum depth point of the sensing area.

Additionally, the end of the guide needle may be inserted to a depth closer to the skin surface than an outmost point of the sensing area.

Further, the guide needle may comprise: an incision portion formed at a front end portion of the guide needle to incise skin of the body in a process in which the guide needle is being inserted into the body, and an insertion support portion formed to be extended from a back portion of the incision portion and configured to be inserted to the body continuously along the incised portion incised by the incision portion, and wherein a boarder point between the insertion support portion and the incision portion is inserted to a depth closer to a surface of the skin than a maximum depth point of the sensing area.

In addition, the applicator may comprise a needle extracting means extracting and removing the guide needle from the body in a state in which the guide needle is inserted to the body, and the needle extracting means may be configured to extract and remove the guide needle before insertion of the sensor module to the body is completed.

Further, the applicator may be configured to insert the sensor module and the guide needle such that the sensor module is inserted faster than the guide needle after the sensor module and the guide needle are inserted into the body.

Additionally, even after the guide needle is inserted to a preset insertion depth in a state that the sensor module may be inserted to the body together with the guide needle, the sensor module is further deeply inserted into the body by the applicator.

Advantageous Effects of Invention

According to an embodiment of the present disclosure, by forming an incised portion by a guide needle so that the incised portion by the guide needle does not cover at least a partial area of a sensing area formed at a sensor module in a state in which a body attachable unit is inserted and attached to a body, the incised portion is not formed adjacent to the sensing area, and accordingly a phenomenon of lowering a blood glucose measurement value caused by the incised portion can be prevented, thereby detecting an accurate blood glucose measurement value from the early stage of operation.

According to an embodiment of the present disclosure, by adjusting an insertion depth of the guide needle through an applicator in a process of inserting and attaching the body attachable unit to the body, a separation distance between the incised portion by the guide needle and the sensing area are adjusted, thereby improving a blood glucose measurement accuracy.

BRIEF DESCRIPTION OF THE DRAWINGS

FIG. 1 is a diagram for schematically illustrating a basic system of a continuous blood glucose measurement apparatus according to an embodiment of the present disclosure.

FIG. 2 is a diagram for schematically illustrating a structure of an applicator of a continuous blood glucose measurement apparatus according to an embodiment of the present disclosure.

FIG. 3 is a diagram for schematically illustrating a body attachable unit of a continuous blood glucose measurement apparatus according to an embodiment of the present disclosure.

FIG. 4 is a diagram for schematically showing structures of a sensor module and a guide needle of a body attachable unit according to a first embodiment of the present embodiment.

FIG. 5 is a diagram for conceptually illustrating a body insertion and attachment process of a body attachable unit according to a first embodiment of the present disclosure.

FIG. 6 is a diagram for conceptually illustrating a body insertion structure of a sensor module and a guide needle according to a first embodiment of the present disclosure.

FIG. 7 is a diagram for conceptually illustrating an arrangement structure of a body incision portion formed by a guide needle and a sensor module according to a first embodiment of the present disclosure.

FIG. 8 is a diagram for conceptually illustrating a body insertion structure of a sensor module and a guide needle according to a second embodiment of the present disclosure.

FIG. 9 is a diagram for conceptually illustrating an arrangement structure of a body incision portion formed by a guide needle and a sensor module according to a second embodiment of the present disclosure.

FIGS. 10 to 12 are diagrams for exemplarily illustrating a structure and an operation state of an applicator for implementing a body insertion form of a sensor module and a guide needle according to a second embodiment of the present disclosure.

DETAILED DESCRIPTION OF EMBODIMENTS

Hereinafter, embodiments of the present disclosure will be described in detail with reference to the accompanying drawings. Throughout this document, reference should be made to the drawings, in which the same reference numerals and symbols will be used to designate the same or like components. Additionally, in the following description of the present disclosure, detailed descriptions of known functions and components incorporated herein will be omitted in the case that the subject matter of the present disclosure may be rendered unclear thereby.

FIG. 1 is a diagram for schematically illustrating a basic system of a continuous blood glucose measurement apparatus according to an embodiment of the present disclosure, FIG. 2 is a diagram for schematically illustrating a structure of an applicator of a continuous blood glucose measurement apparatus according to an embodiment of the present disclosure, and FIG. 3 is a diagram for schematically illustrating a body attachable unit of a continuous blood glucose measurement apparatus according to an embodiment of the present disclosure.

A continuous blood glucose measurement apparatus according to an embodiment of the present disclosure is configured to attach a body attachable unit (20) having a sensor module (520) insertable into a body using an applicator (10) for continuous blood glucose measurement, to insert and attach the body attachable unit (20) to the body by operating or manipulating the applicator (10) to periodically and continuously measure blood glucose from the body, and to transmit blood sugar measurement information periodically measured through the body attachable unit (20) to a separate terminal (30) to output it.

The body attachable unit (20) can be manufactured as a single unit product by being assembled inside the applicator (10), and, in this case, has a structure of which use method is very simple in a shape in which additional work of a user can be minimized when using the continuous blood glucose measurement apparatus. Of course, various manufacturing ways including an example that the body attachable unit (20) is supplied to the user separately from the applicator (10) and the user inserts the body attachable unit (20) into the inside of the applicator (10) to operate it can be implemented.

The body attachable unit (20) may be configured to be attachable to a human body to periodically measure blood sugar level or glucose by extracting body fluid, and transmit the blood glucose measurement result to an external device such as an external terminal (30) and so on. A sensor module (520) of which one end portion can be inserted into the human body and a wireless communication chip (not shown) configured to wirelessly communicate with the external terminal (30) can be disposed inside the body attachable unit (20).

The applicator (10) is formed such that the body attachable unit (20) is fixedly coupled to the inside of the applicator (10), and the applicator (10) is configured to outwardly discharge the body attachable unit (20) according to the user's pressurizing manipulation to a pressurizing button (110).

In this embodiment, the body attachable unit (20) is assembled and produced in a state that the body attachable unit (20) is inserted into the inside of the applicator (10), and is configured to move in an outward discharge direction pursuant to the operation of the applicator (10) by the manipulation of the user and be attached to the human body.

Therefore, a sensor applicator assembly according to an embodiment of the present disclosure is assembled and manufactured in a state that the body attachable unit (20) is inserted in the inside of the applicator (10) at the manufacturing stage and the body attachable unit (20) can be attached to a skin by only the operation of the applicator (10), and because the sensor applicator assembly (1) is supplied to the user in this state, the user can easily attach the body attachable unit (20) to the skin by only the manipulation simply activating the applicator (10) without extra additional operation for attaching the body attachable unit (20) to the skin. Specifically, since the body attachable unit (20) has the wireless communication chip, no connection with an extra transmitter is needed and therefore it can be used more conveniently.

A separate and additional protection cap (200) can be separably coupled to the applicator (10) in order to block external exposure in a state that the applicator (10) is inserted in the inside of the applicator (10), and it may be configured that the user can attach the body attachable unit (20) to the human body by manipulating the applicator (10) after the protection cap (200) is separated and outwardly discharging the body attachable unit (20) toward a position where the protection cap (200) is removed.

In the embodiment of the present disclosure, an adhesive tape (560) is provided at a side of the body attachable unit (20) contacting the human body to be attached to the body, to protect the adhesive tape (560) a release paper (not shown) is attached to a surface of the adhesive tape (560) contacting the human body, and the release paper of the adhesive tape (560) may be configured to be separated and removed from the adhesive tape (560) during the operation of separating the protection cap (200) from the applicator (10).

In a state that the body attachable unit (20) is inserted in the inside, the applicator (10) fixes the body the attachable unit (20), and in a state that the body attachable unit (20) is outwardly discharged and moved, the applicator (10) is configured to release the fixed state of the body attachable unit (20). Accordingly, in a state that the body attachable unit (20) is assembled to be inserted in the inside of the applicator (10), the body attachable unit (20) maintains the fixed state, and when the body attachable unit (20) is externally discharged and attached to the skin by actuating the applicator (10), the state fixed between the applicator (10) and the body attachable unit (20) is released, and therefore if the applicator (10) is separated in this state the applicator (10) is separated from the body attachable unit (20) and only the body attachable unit (20) remains on the skin.

In the body attachable unit (20), the sensor module (520) is disposed in a separate housing (510), and one end portion of the sensor module (520) outwardly protrudes from the bottom surface of the housing (510) so that it can be inserted and attached to the human body. The sensor module (520) may comprise a sensor probe module (521) (See FIG. 5) to be inserted into the human body, and a sensor body module (522) (See FIG. 5) disposed inside the housing (510), and the sensor probe module and the sensor body module are formed as one end portion and another end portion of the sensor unit (520), respectively, and in a bent shape.

In this embodiment, to smoothly perform the body insertion process of the sensor module (520), a separate guide needle (550) may be separatably coupled to the housing (510). The guide needle (550) may surround one end portion of the sensor module (520) and be configured to be inserted together with the sensor module (520) so that one end portion of the sensor module (520) can be stably inserted into the human body.

As shown in FIG. 2, the guide needle (550) may be separatably coupled to the housing (510) in a direction penetrating the top and bottom of the housing (510) of the body attachable unit (20), the guide needle (550) may be formed to have a structure covering the outside of the sensor module (520), and a need head (551) is formed at the upper end portion of the guide needle (550). If the body attachable unit (20) is moved in the direction outwardly discharged by the applicator (10), the guide needle (550) is inserted into the human body first before the sensor module (520) is inserted into the human body and the guide needle (550) may guide the sensor module (520) such that the sensor module (520) can be stably inserted in the skin. The guide needle (550) may be coupled with a needle extracting means (not shown) of the applicator (10) through the needle head (551), and after the body attachable unit (20) is inserted and attached to the human body by the operation of the applicator (10), the guide needle (550) may be configured to be withdrew and removed from the human body by the needle extracting means of the applicator (10).

Next, the details of configurations of the sensor module (520) of the body attachable unit (20) and the guide needle (550) will be followed.

FIG. 4 is a diagram for schematically showing structures of a sensor module and a guide needle of a body attachable unit according to a first embodiment of the present embodiment, FIG. 5 is a diagram for conceptually illustrating a body insertion and attachment process of a body attachable unit according to a first embodiment of the present disclosure, FIG. 6 is a diagram for conceptually illustrating a body insertion structure of a sensor module and a guide needle according to a first embodiment of the present disclosure, and FIG. 7 is a diagram for conceptually illustrating an arrangement structure of a body incision portion formed by a guide needle and a sensor module according to a first embodiment of the present disclosure.

As described above, the sensor module (520) of the body attachable unit (10) comprises a sensor body portion (522) disposed inside the housing (510), and a sensor probe portion (521) bent downward from the sensor body portion (522) and protruded downwardly toward the lower portion of the housing (510). The sensor probe portion (521) is formed to be elongated along a body insertion direction so that at least a part of the sensor probe portion (521) can be inserted into the body, and a sensing area (5211) reacting to blood glucose is formed at an end portion of the sensor probe portion (521) to measure blood glucose in the body. The blood glucose in the body is measured by converting the degree of reaction with blood glucose into an electrical signal through the sensing area (5211) and analyzing it to measure the blood glucose in the body.

The sensor probe portion (521) may be formed in a flat plate shape as shown in FIG. 4, and the sensing area (5211) may be formed on one surface of the sensor probe portion (521) of a flat plate structure.

The guide needle (550) is formed in a shape that surrounds the outside of the sensor probe portion (521), and one side of the guide needle (550) may be formed in a "(=" character channel shape open along a longitudinal direction. Of course, the shape of the guide needle (550) may be formed in the structure which can be various shapes of hollow pipes in which some regions are opened along the longitudinal direction.

The guide needle (550) is configured to guide the insertion of the sensor module (520) into the body and is inserted into the body and incises the body skin before the sensor module (520) is inserted in the process of the guide needle's being inserted into the body together with the sensor module (520), an incision portion (550*a*) is formed at a front end portion of the guide needle (550) and in a structure which can incise the body skin while being inserted into the body, and a insertion support portion (550*b*) which is continuously inserted into the body along a portion incised by the incision portion (550*a*) is extendedly formed at a rear portion of the incision portion (550*a*). The insertion support portion (550*b*) of the guide needle (550) is arrange to surround an outside of the sensor probe portion (521) of the sensor module (520), and the sensing area (5211) formed at an end portion of the sensor probe portion (521) is also arranged such that an outside of the sensing region (5211) is surrounded by the insertion support portion (550*b*) of the guide needle (550).

As described above, the sensor module (520) and the guide needle (550) are coupled to the housing (510) and are inserted and attached to the body skin by the applicator (10), and after the sensor module (520) and the housing (510) are attached to the body skin, the guide needle (550) is drawn and removed from the body skin by the applicator (10).

At this time, as illustrated in FIG. 5(*a*), an insertion depth (ND) of the guide needle (550) is formed to be deeper than an insertion depth (SD) of the sensor module (520) according to the arrangement relationship of the sensor module (520) and the guide needle (550). Because the insertion support portion (550*b*) of the guide needle (550) is arranged to surround the sensor module (520), an insertion depth (ND) of an end of the incision portion (550*a*) of the guide needle (550) is also formed to be deeper than the insertion depth (SD) of the sensor module (520). The guide needle (550) incises body skin (E) and leaves cut in the body skin (E), and if the guide needle (550) is drawn and removed after the guide needle (550) is inserted into the body, the portion of the body skin (E) incised by the guide needle (550) has the same depth as the insertion depth (ND) of the guide needle (550).

In this way, when looking into details of the arrangement relationship between the portion incised by the guide needled (550) in the body skin (E) and the sensor module (520) after the guide needle (550) is drawn out and removed from the body skin (E), an incised portion (CA) by the guide needle (550) is formed to be spaced apart from both sides of the sensor module (520) based on a vertical cross-section of the body skin (E) as shown in FIG. 7. At this time, when the separation distance between the sensor module (520) and the guide needle (550) is very small or in a non-spaced contact state, the incised portion (CA) by the guide needle (550) in the body skin (E) may be formed in contact with the sensor module (520).

The incised portions (CA) formed on both sides of the sensor module (520) in the body skin (E), respectively, are substantially formed by inserting the insertion support portion (550*b*) of the guide needle (550), and the incised portion formed by the incision portion (550*a*) of the guide needle (550) may be formed to extend deeper in an oblique direction from the incised portion (CA) by the insertion support portion (550*b*) as illustrated by a dotted line in FIG. 7. The depth of the incised portion (CA) formed by the incision portion (550*a*) of the guide needle (550) is ND, the depth of the incised portion (CA) formed by the insertion support portion (550*b*) of the guide needle (550) is ND1, and in this case, the insertion depth of the sensor module (520) is SD.

Accordingly, around a peripheral portion of the sensing area (5211) formed on one surface of the sensor probe portion (521) of the sensor module (520), the incised portion (CA) formed by the insertion support portion (550*b*) of the guide needle (550) is formed in a structure of surrounding an outside of the sensing area (5211).

Because the incised portion (CA) formed by the guide needle (550) is a wound in the body, a small amount of bleeding occurs at the incised portion (CA) and at the same time, white blood cells (BC) due to the body's immune response are gathered to the incised portion (CA) as shown in the enlarged view of FIG. 7. As such, if the white blood cells (BC) are gathered into the incised portion (CA), the blood glucose response amount is changed in the sensing area (5211) of the sensor module (520) positioned nearby, thereby lowering blood glucose measurement accuracy.

Accordingly, when the white blood cells (BC) are gathered to the incised portion (CA) formed by the guide needle (550) after the guide needle (550) is withdrawn and removed, adjacent blood glucose substance (glucose) is coupled with the white blood cells (BC), and accordingly, the reaction amount of the blood glucose substance reacting with the sensing area (5211) may be reduced. As such, a blood glucose measurement value measured by the sensor module (520) is not a blood glucose measurement value which is in a normal state, but a substantially lowered value due to the reduction of the blood glucose substance reacting with the sensing area (5211) caused by the concentration of the white blood cells (BC). This change in the blood glucose measurement amount due to the influence of the white blood cells (BC) may continue for several days until all the incised portions (CA) are recovered.

Therefore, because the guide needle (550) is inserted into the body together with the sensor module (520), in the body attachable unit (10) of the continuous blood glucose measurement apparatus, a phenomenon in which the accuracy of blood glucose measurement is deteriorated due to the incised wound formed by the guide needle (550) at an initial stage operation of starting to attaching the body attachable unit (10) occurs.

Hereinafter, a structure for minimizing a phenomenon of decrease in blood glucose measurement accuracy described above will be described.

FIG. 8 is a diagram for conceptually illustrating a body insertion structure of a sensor module and a guide needle according to a second embodiment of the present disclosure, and FIG. 9 is a diagram for conceptually illustrating an arrangement structure of a body incision portion formed by a guide needle and a sensor module according to a second embodiment of the present disclosure.

The sensor module (520) and the guide needle (550) according to the second embodiment of the present disclosure are formed in structures in which the guide needle (550) surrounds an outside of the sensor probe portion (521) as described above.

In the body insertion process, the guide needle (550) is inserted prior to or at the same time as the insertion of the sensor module (520), and is removed by the applicator (10) after being inserted into the body. In order for the guide needle (550) to be inserted into the body prior to or at the same time as the insertion of the sensor module (520), an end of the guide needle (550) protrudes so as to be positioned closer to the body skin (E) than an end of the sensor module (520) in an area before insertion to the body as illustrated in FIG. 8(*a*).

At this time, the guide needle (550) according to the second embodiment of the present disclosure is inserted in a way that the incised portion (CA) in the body, incised by the guide needle (550), does not cover at least a part of the sensing area (5211) at the outside of the sensor module (520).

For example, in a state in which the body insertion process of the sensor module (520) and the guide needle (550) is completed as shown in FIGS. 8(*b*) and 8(*c*), the guide needle (550) may be inserted in the body skin (E) so that the insertion depth (ND) of the guide needle (550) is less than the insertion depth (SD) of the sensor module (520). That is, the guide needle (550) may be inserted to a shallower depth than the sensor probe portion (521) of the sensor module (520). Thereafter, the guide needle (550) is removed from that depth without being inserted deeper in the state shown in FIGS. 8(*b*) and 8(*c*).

More specifically, as shown in FIG. 8(*b*), the guide needle (550) can be inserted into a depth in which an insertion depth (ND) of an end of the guide needle (550) is positioned closer to the skin surface than an outmost point (5211*a*) of the sensing area (5211), but, unlike this, as illustrated in FIG. 8(*c*), the guide needle (550) can be inserted to a depth in which an insertion depth (ND) of an end of the guide needle (550) is positioned closer to the skin surface than a maximum depth point (5211*b*) of the sensing area (5211). After being inserted to this depth, the guide needle (550) is drawn out and removed from the skin, and the incised portion (CA) formed by the insertion of the guide needle (550) is left as a wound inside the skin (E).

Because the incised portion (CA) is formed in the body skin (E) along the body skin insertion path of the guide needle (550), the incised portion (CA) incised by the guide needle (550) is also formed to have a shallower depth than inside the body the sensor probe portion (521) when the guide needle (550) is inserted to a shallower depth than the sensor probe portion (521).

When the incised portion (CA) incised by the guide needle (550) is formed to have a shallower depth than the sensor probe portion (521), the incised portion (CA) is not formed around an adjacent area facing the sensing area (5211) as shown in FIG. 9, and because white blood cells (BC) concentrated in the incised portion (CA) do not exist at a position adjacent to the sensing area (5211), the loss of the blood glucose substances due to the white blood cells (BC) can be reduced around the sensing area (5211), thereby further improving the accuracy of a blood glucose measurement value through the sensing area (5211).

Accordingly, as the incised portion (CA) formed by the guide needle (550) is minimized in the adjacent area facing the sensing area (5211), that is, the incised area (CA) formed by the guide needle (550) is located further away from the sensing area (5211), the loss of blood glucose substances by the white blood cells (BC) in the vicinity of the sensing region (5211) decreases, thereby obtaining a more accurate blood glucose measurement value.

As illustrated in FIG. 9, when looking at the incised portion (CA) formed by the guide needle (550) with respect to a vertical cross-section of the body skin (E), the incised portion (CA) formed by the insertion support portion (550*b*) of the guide needle (550) is formed at both sides of the sensor probe portion (521), and the incised portion (CA) formed by the incision portion (550*a*) of the guide needle (550) may be formed to extend in an oblique direction from an end of the incised portion (CA) formed by the insertion support portion (550*b*) as illustrated by a dotted line.

Accordingly, the incised portion (CA) formed by the insertion support portion (550*b*) is formed to face the sensing area (5211) at an area more adjacent to the sensing area (5211) than the incised portion (CA) formed by the incision portion (550*a*) of the guide needle (550), and therefore the incised portion (CA) formed by the insertion support portion (550*b*) affects more the loss of the blood glucose substance by the white blood cells (BC) in the vicinity of the sensing region (5211). Accordingly, a degree in which the incised portion (CA) formed by the insertion support portion (550*b*) is away from the sensing region (5211) greatly affects the blood glucose measurement accuracy.

When the insertion depth (ND) of the end of the incision portion (550*a*) of the guide needle (550) is positioned closer to the skin surface than the outermost point (5211*a*) of the sensing region (5211) (if positioned shallower), as shown in FIG. 9(*a*), the depth (ND) to the end of the incised portion (CA) formed by the incision portion (550*a*) is positioned shallower than the outermost point (5211*a*) of the sensing area (5211), and in this case, since the depth (ND1) of the incised portion (CA) formed by the insertion support portion (550*b*) is positioned shallower than the depth (ND) to the end of the incised portion (CA) formed by the incision portion (550*a*), the incised portions (CA) formed by the incision portion (550*a*) and the insertion support portion (550*b*) of the guide needle (550) are more adjacent to the skin surface and are away from the sensing area (5211) in a form that the incised portions (CA) formed by the incision portion (550*a*) and the insertion support portion (550*b*) of the guide needle (550) do not surround an outside of the sensing area (5211) at all. Therefore, because the incised portion (CA) does not exist in a region adjacent to the sensing area (5211), the white blood cells concentrated to the incised portion (CA) are relatively far from the sensing area (5211). Hence, because the loss of blood glucose substances by the white blood cells (BC) hardly occurs in the sensing area (5211), a more accurate blood sugar measurement value can be obtained.

In addition, when the insertion depth (ND) of the end of the incision portion (550*a*) of the guide needle (550) is located between the outermost point (5211*a*) and the maximum depth point (5211*b*) of the sensing area (5211), as shown in FIG. 9(*b*), the depth (ND) to the end of the incised portion (CA) formed by the guide needle (550) is positioned shallower than the maximum depth point (5211*b*) of the sensing area (5211), and the depth (ND1) of the incised portion (CA) formed by the insertion support portion (550*b*) of the guide needle (550) may be positioned shallower or deeper than the position of the outermost point (5211*a*) of the sensing area (5211). In this case, the incised portion (CA) formed by the incision portion (550*a*) of the guide needle (550) or the incised portion (CA) formed by the insertion support portion (550*b*) is formed in a shape of surrounding a portion of an outside of the sensing area 5211 (that is, another portion of the sensing area (5211) is not covered from the outside by the incised portion (CA)), and accordingly, because the incised portion (CA) of the guide needle (550) does not surround a whole area of the sensing area (5211), the loss of blood glucose substances by the white blood cells (BC) generated in the vicinity of the sensing region 5211 can be significantly reduced, thereby relatively improving the accuracy of a blood glucose measurement value.

In this way, the insertion depth of the guide needle (550) is formed to be shallower than the depth of the sensor probe portion (521), so that the incised portion (CA) formed by the guide needle (550) does not cover at least a partial area of the sensing area (5211), and therefore a phenomenon of decreasing blood glucose substances due to white blood cells (BC) generated at the incised portion (CA) can be minimized, thereby further improving the measurement accuracy of the sensing region (5211).

Next, configurations for adjusting insertion depths of the sensor module (520) and the guide needle (550) of the body attachment unit (10) related to each other, described above, will be described.

FIGS. 10 to 12 are diagrams for exemplarily illustrating a structure and an operation state of an applicator for implementing a body insertion form of a sensor module and a guide needle according to a second embodiment of the present disclosure.

The applicator (10) according to an embodiment of the present disclosure is a device that operates to insertly attach the body attachable unit (10) to the body by the user's manipulation as described above, and can be configured to comprise a main case (100) with one open side, a plunger body (300) configured to move in a direction of being outwardly discharged from the inside of the main case (100) toward the open side, and a plunger elastic spring (S1) applying an elastic force to the plunger body (300) in a direction in which the plunger body (300) is outwardly discharged, and the body attachable unit (10) is coupled to the plunger body (300) and can be configured to move in a direction of being outwardly discharged together with the plunger body (300).

A manipulation or operation part such as a pressing button (not shown) that a user can manipulate is provided on the outside of the main case (100), the plunger body (300) is coupled and fixed to a first position inside the main case (100), the coupling and fixing are released from the first position according to the manipulation of the manipulation or operation part, and the plunger body (300) is linearly moved to a second position, which is in an outward discharge direction, by the elastic force of the plunger elastic spring (S1). The body attachable unit (10), which is coupled to one end of the plunger body (300), linearly moves in the outward discharge direction and is inserted and attached to the body skin (E) together with the plunger body (300).

The body attachable unit (10) includes a housing (510), a sensor module (520) including a sensor body portion (522) and a sensor probe portion (521), and a guide needle (550) arranged to surround an outside of the sensor probe portion (521) and separatably coupled to the housing (510).

When the body attachable unit (10) is outwardly discharged, the sensor probe portion (521) of the sensor module (520) is arranged to outwardly protrude from the bottom surface of the housing (510) so that the sensor probe portion (521) is inserted into the body skin (E), and the guide needle (550) surrounds an outside of the sensor probe portion (521) and is inserted into the body skin (E) together with the sensor probe portion (521).

After the guide needle (550) is inserted into the body skin (E), the guide needle (550) is extracted and removed from the skin (E), and the applicator (10) comprises a needle extracting means (N) withdrawing and removing the guide needle (550) from the body skin (E) in a state that the guide needle (550) is inserted to the body skin (E).

The needle extracting means (N) is engaged with the plunger body (300) and can be configured to comprise a needle extracting body (400) coupled with a needle head (551) formed at an upper portion of the guide needle (550), and a needle extracting elastic spring (S2) applying an elastic force to the needle extracting body (400) in a direction opposite to the outward discharge direction. A hook engaging portion (350) capable of constraining the elastic movement of the needle extracting body (400) is formed at the plunger body (300), and an elastic hook (410) engaging with the hook engaging portion (350) is formed at the upper portion of the needle extracting body (400). The elastic hook (410) is engaged with the hook engaging portion (350) so that the needle extracting body (400) is integrally moved together with the plunger body (300) in the outward discharge direction, when it moves by a preset distance, the engagement state between the elastic hook (410) and the hook engaging portion (350) is released by a separate catch release means (not shown), and in this state, the needle extracting body (400) is moved in a direction opposite to the outward discharge direction by the needle extracting elastic spring (S2).

At this time, the needle extracting means (N) can be configured to withdraw and remove the guide needle (550) from the body skin (E) before the insertion of the sensor module (520) to the body skin (E) is completed as illustrated in FIG. 10, and through this, the sensor module (520) may be inserted deeper into the body skin (E) than the guide needle (550).

In more detail, in the state shown in FIG. 10(*a*), when the manipulation or operation part of the applicator (10) is manipulated by the user, the housing (510) of the body attachable unit (10) moves together with the plunger body (300) from the first position (an inner upper region) inside the main case (100) to a second position (an inner lower region) in the outward discharge direction as illustrated in FIGS. 10(*b*) and 10(*c*), and the sensor probe portion (521) of the sensor module (520) moves together with the plunger body (300) and the housing (510) to the second position, and is inserted into the body skin (E) by a preset insertion depth SD as shown in FIG. 10(*c*).

At this time, during the middle of the process that the guide needle (550) is moving together with the plunger body (300) and the housing (510) toward the second position, the guide needle (550) is moved toward the first position by the needle extracting means (N) at a third position, which is a middle region, to be removed from the body as shown in FIG. 10(*b*). That is, when the guide needle (550) together with the plunger body (300) and the housing (510) reaches the third position, the engaged status between the elastic hook (410) of the needle extracting body (400) and the hook engaging portion (350) of the plunger body (300) is released, and at the same time, the needle extracting body (400) performs an upward return movement toward the first position by the elastic force of the needle extracting elastic spring (S2), and in this process, the guide needle (550) moves upward together with the needle extracting body (400) and is removed from the body skin (E).

In summary, after the guide needle (550) is inserted into the body skin (E) before the insertion of the sensor module (520) and guides the insertion of the sensor module (520) in the process that the guide needle (550) penetrates and is inserted into the body skin (E) from the outside, the guide needle (550) does not move to the second position with the sensor module (520), and the guide needle (550) is extracted and removed from the body by upwardly moving toward the first position by the needle extracting means (N) at the third position which is the middle region, that is, in a state that the guide needle (550) is inserted by a depth ND which is less than an insertion depth SD of the sensor module (520).

Therefore, in a state that the insertion and attachment of the body attachable unit (10) to the body skin (E) are finally completed, the sensor module (520) is inserted by a depth SD as shown in FIG. 10(*c*), and the guide needle (550) is inserted by a depth ND less than SD. The insertion depth (ND) of the guide needle (550) may be set to various depths according to the user's needs.

On the other hand, as shown in FIG. 11, the sensor module (520) and the guide needle (550) are inserted into the body skin (E) by the applicator (10) such that the sensor module (520) is inserted faster than the guide needle (550) at a region after being inserted into the body skin (E), and through this, the sensor module (520) can be inserted deeper into the body skin (E) than the guide needle (550).

For this purpose, a separate rack and pinion gear structure may be used. For example, a housing rack gear (T3) is formed on both sides of the housing (510) along the outward discharge direction, and a case rack gear (T2) is formed at the lower portion of the inner surface of the main case (100) of the applicator (10) along the outward discharge direction. A pinion gear (T1) interlockedly coupled to both the housing rack gear (T3) and the case rack gear (T2) is rotatably coupled to one side of the plunger body (300). The plunger body (300) and the housing (510) are arranged so that the pinion gear (T1) and the housing rack gear (T3) are meshed with each other as shown in FIG. 11(*a*) in a state before the operation of the applicator (10).

According to this structure, when the manipulation or operation part of the applicator (10) is manipulated by the user, the plunger body (300) and the housing (510) move integrally from a state shown in FIG. 11(*a*) to a state shown in FIG. 11(*b*), and the guide needle (550) begins to be inserted into the body skin (E). In this state, the pinion gear (T1) starts to mesh with the case rack gear (T2) too. Thereafter, as shown in FIG. 11(*c*), when the plunger body (300) continues to move to the second position in the outward discharge direction, the pinion gear (T1) is rotated by the engagement with the case rack gear (T2) in this process, and the housing rack gear (T3) is moved in the outward discharge direction (downward) by the rotation of the pinion gear (T1). That is, in a section from a state shown in FIG. 11(*b*) to a state shown in FIG. 11(*c*), when the plunger body (300) moves downward, the pinion gear (T1) is rotated by the case rack gear (T2), and the housing rack gear (T3) is moved downward by the rotation of the pinion gear (T1).

As such, the housing rack gear (T3) moves downward in a section from FIG. 11(*b*) to FIG. 11(*c*), and therefore, the housing (510) moves downward together with the housing rack gear (T3). Accordingly, in this section, the housing (510) moves downward at a speed of the total of a basic speed (v1: a speed of moving downward by the plunger elastic spring (S1)) of moving downward together with the plunger body (300) and an additional downward movement speed (v2: a speed of moving downward together with the housing rack gear (T3)). At this time, because the sensor module (520) is coupled to the housing (510) and moves integrally together with the housing (510), the sensor module (520) moves at the same downward movement speed as the downward movement speed (v1+v2) of the housing (510), but the guide needle (550) moves downward at the same downward movement speed (v1) as that of the plunger body (300) by the needle extracting body (400) constrained to the plunger body (300).

Therefore, from a time point when the guide needle (550) starts to be inserted into the body skin (E), the body insertion speed (v1+v2) of the sensor module (520) is higher than the body insertion speed (v1) of the guide needle (550), and accordingly, the insertion depth (SD) of the sensor module (520) is formed to be deeper than the insertion depth (ND) of the guide needle (550) finally as shown in FIG. 11(*c*).

As such, when the insertion movement of the guide needle (550) and the sensor module (520) is completed, the engagement between the elastic hook (410) of the needle extracting body (400) and the plunger body (300) of the hook engaging portion (350) is released, and therefore, the guide needle 550 is extracted and removed from the body skin (E) by the needle extracting means (N).

On the other hand, as shown in FIG. 12, even after the guide needle (550) is inserted by a preset insertion depth in a state that the sensor module (520) is inserted to the body skin (E) together with the guide needle (550), the sensor module (520) can be further inserted by being configured to be inserted into the body skin (E) by the applicator (10), and through this, the sensor module (520) may be inserted deeper into the body skin (E) than the guide needle (550).

For this purpose, a separate spring and rotation link may be used. For example, a housing spring (S3) capable of elastically moving the housing (510) coupled to the plunger body (300) in the outward discharge direction is disposed in the space between the plunger body (300) and the housing (510), and a rotation locking link (LK) capable of constraining the downward movement of the housing (510) from the plunger body (300) and releasing the constraining may be rotatably coupled to the plunger body (300). As illustrated in FIG. 12(*a*), the rotation locking link (LK) maintains a status that its outer side portion is in close contact with an inner side of the main case (100) of the applicator (10) and therefore its rotation is constrained. An operation groove (LH) of a concavely recessed shape is formed on an end portion of the inner surface of the main case (100) in the outward discharge direction, and the constraining of the rotation of one end of the rotation locking link (LK) is released by the operation groove (LH).

According to this structure, when the manipulation or operation part of the applicator (10) is manipulated by the user, the plunger body (300) and the housing (510) are outwardly discharged by the plunger elastic spring (S1) in the state shown in FIG. 12(*a*), and because in this process the rotation of the rotation locking link (LK) is constrained by the rotation locking link's (LK's) being in close contact with the inside surface of the main case (100), the movement of the housing (510) is constrained by the rotation locking link (LK) and therefore the housing (510) does not move relative to the plunger body (300) and moves downward integrally together with the plunger body (300). Thereafter, when the outward discharge movement of the plunger body (300) is completed as shown in FIG. 12(*b*), the rotation locking link (LK) reaches an operation groove (LH) area, and accordingly, the constraining of the rotation of the rotation locking link (LK) is released. Therefore, as shown in FIGS. 12(*b*) and 12(*c*), the rotation locking link (LK) rotates, and accordingly, the constraining of the housing (510) is released and accordingly the housing (510) further moves downward by the housing spring (S3).

At this time, the sensor module (520) moves integrally together with the housing (510) and is further inserted into the body skin (E). In a state that the downward movement of the plunger body (300) is completed regardless of the further downward movement of the housing (510), the guide needle (550) is withdrawn and removed from the body skin (E) by the needle extracting means (N) by releasing the engagement between the elastic hook (410) of the needle extracting body (400) and the hook engaging portion (350) of the plunger body (300) as shown in FIG. 12(*b*).

Accordingly, when the operation of attaching and inserting the body attachable unit (10) into the body according to the operation of the applicator (10) is completed, as shown in FIGS. 12(*b*) and 12(*c*), the guide needle (550) moves integrally with the plunger body (300), and, after being inserted by a insertion depth ND, the guide needle (550) is extracted and removed, and thereafter, the sensor module 520 is further moved downward together with the housing (510), thereby being further inserted by a depth SD deeper than a depth ND inside the body skin (E).

The configuration related to the adjustment of the insertion depth of the sensor member (520) and the guide needle (550) described above is exemplary, and may be changed and applied in various other ways.

The foregoing descriptions have been presented in order to explain certain principles of the present disclosure by way of example, and a person having ordinary skill in the art which the present disclosure relates could make various modifications and variations without departing from the essential features of the present disclosure. Accordingly, the foregoing embodiments disclosed in the present disclosure shall be interpreted as being illustrative, while not being limitative, of the principle and scope of the present disclosure. It should be understood that the scope of the present disclosure shall be defined by the Claims and all of their equivalents fall within the scope of the present disclosure.

What is claimed is:

1. A continuous glucose measurement apparatus comprising:

a body attachable unit configured to be insertedly attachable to a body to periodically measure blood glucose; and an applicator configured to insert and attach the body attachable unit to the body according to manipulation of a user, wherein the body attachable unit comprises:

a housing, a sensor module configured to be insertable into the body, wherein a sensing area to react with the blood glucose in the body is formed at one side of the sensor module, and a guide needle arranged to cover an outside of the sensor module, and configured to, after being inserted into the body together with the sensor module, be extracted and removed from the body, wherein the applicator comprises:

a main case, a plunger body disposed inside the main case and configured to move in an outward discharge direction along with the body attachable unit, and a rack and pinion gear structure configured to move only the sensor module in the outward discharge direction relative to the guide needle while the guide needle is being inserted into the body, to insert the sensor module deeper into the body than the guide needle, and wherein the rack and pinion gear structure comprises:

a housing rack gear formed on an outer side of the housing, a case rack gear formed on an inner side of the main case, and a pinion gear rotatably coupled to one side of the plunger body.

2. The continuous glucose measurement apparatus of claim 1, wherein, in a body insertion process, the guide needle is inserted to the body before or at the same time as the sensor module is inserted to the body.

3. The continuous glucose measurement apparatus of claim 2, wherein the sensor module comprises a sensor probe portion formed to be elongated along a body insertion direction so that at least a partial section of the sensor probe portion is insertable into the body, and the sensing area is formed at an end part of the sensor probe portion.

4. The continuous glucose measurement apparatus of claim 3, wherein the guide needle has a shape of covering an outside of the sensor probe portion, and the guide needle is configured to be extracted and removed from the body after being inserted to a shallower depth than the sensor probe portion.

5. The continuous glucose measurement apparatus of claim 4, wherein an end of the guide needle is inserted to a depth closer to a skin surface than a maximum depth point of the sensing area.

6. The continuous glucose measurement apparatus of claim 5, wherein the end of the guide needle is inserted to a depth closer to the skin surface than an outmost point of the sensing area.

7. The continuous glucose measurement apparatus of claim 4, wherein the applicator comprises a needle extracting means extracting and removing the guide needle from the body in a state in which the guide needle is inserted to the body, and the needle extracting means is configured to extract and remove the guide needle before insertion of the sensor module to the body is completed.

8. The continuous glucose measurement apparatus of claim 4, wherein the applicator is configured to insert the sensor module and the guide needle such that the sensor module is inserted faster than the guide needle after the sensor module and the guide needle are inserted into the body.

9. The continuous glucose measurement apparatus of claim 4, wherein, even after the guide needle is inserted to a preset insertion depth in a state that the sensor module is inserted to the body together with the guide needle, the sensor module is further deeply inserted into the body by the applicator.

10. The continuous glucose measurement apparatus of claim 3, wherein the guide needle comprises:

an incision portion formed at a front end portion of the guide needle to incise skin of the body in a process in which the guide needle is being inserted into the body, and an insertion support portion formed to be extended from a back portion of the incision portion and configured to be inserted to the body continuously along an incised portion, the incised portion being a wound in the body formed by the incision portion, and wherein one end of the incision portion is inserted to a depth closer to a surface of the skin than a maximum depth point of the sensing area.

* * * * *